United States Patent [19]  [11]  4,346,188
Costanzi et al.  [45]  Aug. 24, 1982

[54] POLYOLEFIN COMPOSITIONS STABILIZED AGAINST UV-RADIATIONS BY PYRROLIDINE DERIVATIVES

[75] Inventors: Silvestro Costanzi, San Giuliano Milanese; Francesco Tessarolo, Monza; Adriano Ballabio, Giussano; Maurizio Brunelli, Milan, all of Italy

[73] Assignee: ANIC, S.p.A., Palermo, Italy

[21] Appl. No.: 213,655

[22] Filed: Dec. 5, 1980

[30] Foreign Application Priority Data

Feb. 19, 1980 [IT] Italy ................................ 20002 A/80

[51] Int. Cl.$^3$ ...................... C08K 5/00; C07D 207/08
[52] U.S. Cl. ................................ 524/104; 260/326.2; 260/326.25; 524/583; 524/585
[58] Field of Search ........... 260/45.8 N, 326.2, 326.25

[56] References Cited

U.S. PATENT DOCUMENTS 4,111,901  9/1978  Hechenbleikner ............ 260/45.8 N

Primary Examiner—Jane T. Fan
Attorney, Agent, or Firm—Morgan, Finnegan, Pine, Foley & Lee

[57] ABSTRACT

Polyolefin polymers can successfully be stabilized against the detrimental effects of UV-radiations by compounding them with a stabilizer belonging to the class of compounds containing a pyrrolidine ring and which are sterically hindered in the 3-position and also substituted in such position by substituents having a high molecular weight. The esters of the 2,2,5,5-tetraalkyl-4-methyl-3-methylol pyrrolidine are exemplary compounds; the adipic and the stearic esters are preferred.

7 Claims, No Drawings

POLYOLEFIN COMPOSITIONS STABILIZED AGAINST UV-RADIATIONS BY PYRROLIDINE DERIVATIVES

This invention relates to novel polyolefin compositions which are stabilized against the noxious action of UltraViolet radiations by incorporating therein certain pyrrolidine derivatives the ring structure of which is strongly sterically hindered in the "3" position.

As is known, polyolefins, and more particularly polypropylene and polyethylene, are subjected to degradation in time by exposure to weathering agents, more particularly to the action of UV-radiations.

Such a degradation is denounced by a decay of the physical properties of the articles, such as decrease of the tensile strength and of pliability. This decay of the properties of the polymers is manifested by a pronounced rise of the viscosity index of the melted polymer, that is, the Melt Flow Index, MFI.

Thus, the determination of the trend of the MFI values subjected to exposure to degrading agents, such as UV-radiations, furnishes an indication of the intensity of the polymer degradation.

In order to counteract the deterioration of the polyolefins and to offset the decay of their physical properties, it has been common practice to incorporate in the polymer mass small amounts of stabilizing compounds of such a nature that they do not jeopardize the other intrinsic properties of the polymers.

It has now been found, and this is the subject matter of the present invention, that chemical compounds which contain a pyrrolidine ring and which are sterically hindered in the 3-position and also substituted in such position by substituents having a high molecular weight, possess quite excellent stabilizing properties against the noxious action of UV-radiations for polyolefins such as polyethylene and polypropylene. The preparation of such compounds will be described hereinafter.

The products which can be employed in the present invention are esters of 2,2,5,5-tetraalkyl-4-methyl-3-methylol-pyrrolidine, which can be obtained by mono- or di-esterification of pyrrolidine with mono- or di-carboxylic acids which contain a chain of at least six carbon atoms, and which have the general formula:

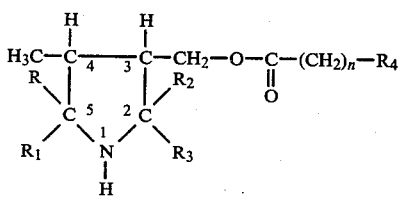

wherein:

$R, R_1, R_2$ and $R_3$ are alkyl radicals which can be the same, or different from each other, $R_4$ can be hydrogen or an alkyl radical, or a carboxyester, the esterified group which contains the pyrrolidine ring, and n is greater than or equal to zero, with the exception of the case in which $R_4$ is a hydrogen when n is greater than or equal to one.

The starting product for the preparation of such compounds can be obtained by a process which is simple to carry out and is disclosed in copending U.S. patent application Ser. No. 149,511, filed May 13, 1980 by Silvestro Costanzi et al. The process comprises the step of cyclizing di-tert.proparglyamines in an acidic environment with a catalyst being optionally present, whereby 4-methyl-2,2,5,5-tetraalkyl-3-formyl-3-pyrrolidines are obtained and which are subsequently hydrogenated in order to prepare the corresponding 3-methylol-pyrrolidine derivatives.

To form the stabilizing pyrrolidine esters of the present invention, the methylol derivative concerned is esterified with a mono- or a bicarboxylic acid (possibly esterified) to form the stabilizing pyrrolidine coming within the foregoing formula.

The syntheses of a few pyrrolidine esters of the kind referred to hereinabove will now be described, along with their practical applications as anti-UV stabilizers for polypropylene articles.

EXAMPLE 2,2,4,5,5-pentamethyl-3-formyl pyrrolidine was prepared in accordance with the procedures disclosed in the aforementioned U.S. patent application Ser. No. 149,511, by reacting the di-tert.propargylamine, having the formula:

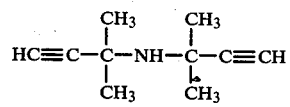

with conc.sulfuric acid at a temperature in the range 125° C.–130° C. for about 1½ hrs, using 50 g of the amine in 140 mls water and 220 mls of 96%-$H_2SO_4$ having a specific gravity of 1.8. The recrystallized reaction product was then hydrogenated as follows.

20 grams of the thusly obtained pentaalkylformyl-pyrroline were introduced into an autoclave together with 50 mls ethanol and 2 g of a Pd-catalyst supported on activated charcoal. The reaction mixture was reacted at room temperature, with stirring, under a hydrogen pressure of approximately 5 bars.

On completion of the hydrogenation step, the catalyst was filtered off, and the product distilled. It is a colorless liquid having a b.p. of 90° C.–91° C. under an abs. pressure of 1 mmHg (millimeters of mercury).

20 grams of the resultant pentaalkyl-formyl-pyrrolidine were dissolved in 40 mls of ethanol in a flask fitted with a stirrer and a dropping funnel and a solution consisting of 50 mls of water, 10 g of NaOH and 2 g of NaBH$_4$ slowly introduced into the flask.

The reaction mixture was maintained at room temperature for 3 hours after which the excess of sodium borohydride was destroyed with diluted HCl.

The reaction mixture was eventually made alkaline with a solution of caustic soda and extracted with ethyl ether. The organic layer was dried and evaporated, the result being a white solid residue having a m.p. of 90° C.–91° C., the structure of which, corresponds; to 2,2,4,5,5-pentamethyl-3-methylol-pyrrolidine, as confirmed by InfraRed analysis, NMR analysis and mass spectrography.

The product which was obtained was esterified with adipic and stearic acid, respectively, according to conventional procedures as follows.

Preparation of adipoyl-bis-(2,2,4,5,5-pentamethyl-pyrrolidine-3-methylol)-ester

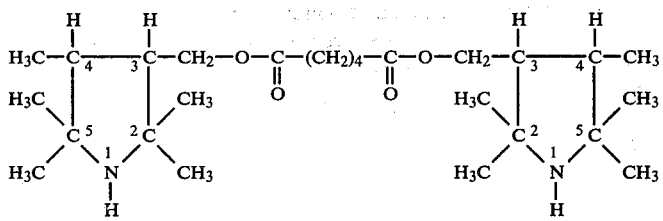

A flask of appropriate capacity was charged with 10 g of 2,2,4,5,5-pentamethyl-3-methylolpyrrolidine, 40 mls of xylene and 0.5 g of sodium methylate. Through a specially provided dropping funnel, 5 g of dimethyl adipate, dissolved in xylene, was added thereto.

The solution was heated to 160° C. and was maintained at that temperature for approximately 12 hours, the xylene-methanol mixture being continually removed and a concurrent addition of an equivalent volume of fresh xylene being effected.

On completion of the reaction, the mixture was poured in water and the organic layer was separated and fractionated. The product obtained, the structure of which has been confirmed by mass spectrography and NMR analysis, had, at room temperature, the appearance of a viscous liquid and was a light straw-yellow color, having a b.p. of 215° C.–220° C. under an abs.-pressure of 0.1 mmHg.

Preparation of 2,2,4,5,5-pentamethyl-pyrrolidine-3-methylol stearate

This ester was prepared by reacting 10 g of pentamethyl-3-methylol-pyrrolidine with 17 g of methyl stearate.

The two esters, adipic and stearic acid ester, respectively, prepared according to the procedure outlined above, were used as anti-UV stabilizers for polypropylene and compared with commercially available stabilizing agents, viz.: benz-triazole (Tinuvin P, Trade Mark), a derivative of tetramethyl-piperidine (Tinuvin, Trade Mark) and benzophenone (Tinuvin 531, Trade Mark).

To perform the comparative tests, a General Purpose polypropylene, already compounded with the usual stablizers and compounding ingredients, was supplemented with 0.5% by wt of the adipoyl-bis(2,2,4,5,5-pentamethyl-pyrrolidine-3-methylol)-ester (1), with 0.9% by wt of the stearate of 3-methylol-2,2,4,5,5-pentamethyl pyrrolidine(2), with 0.5% by wt of benz-triazole, with 0.5% of a tetramethylpiperidine derivative and with 0.5% by wt of benzophenone, respectively.

Mixing was accomplished according to the usual procedures for incorporating stabilizers into polyolefin compounds, that is by 5-minute milling on a roller mill at 180° C.

Thereafter, platelets having a thickness of 0.5 mm were prepared in a compression press at 180° C. with a processing cycle consisting of a 5-minute preheating period and a 5-minute compression period.

Platelets of non-stabilized polypropylene were similarly prepared.

The so prepared platelets were exposed in an Atlas Weatherometer (Trade Mark) having two arc lamps with emission peaks at 3,600, 3,850 and 4,200 Ångstrom Units, while adopting a rain cycle consisting of 102 mins. of irradiation and 18 mins. of rain.

The resistance of the polypropylene samples to the UV-exposure was assessed by viscosity measurements, and more exactly by measuring the Melt Flow Index, MFI, according to the prescriptions contained in the ASTM D-1238 specifications over several exposure time periods.

The test results are set forth in the following Table.

| Melt Flow Index Trend General Purpose Polypropylene with various anti-UV stabilizers | | | | | | |
|---|---|---|---|---|---|---|
| Exposure time, hours | 0 Start | 500 | 750 | 1,000 | 1,250 | 1,800 |
| POLYPROPYLENE, as such | 3.8 | 4.8 | 5.7 | 7 | 9 | >50 |
| POLYPROPYLENE + 0.5% of (1) (adipic ester) | 3.7 | 6 | 5.5 | 5 | 5.2 | 5.8 |
| POLYPROPYLENE + 0.9% of (2) (stearate) | 3.9 | 5.5 | 6 | 6 | 6.5 | 6.8 |
| POLYPROPYLENE + 0.5% benz-triazole (commercial) | 3.6 | 5.1 | 5.2 | 6 | 6.5 | 22 |
| POLYPROPYLENE + 0.5% deriv. of tetramethylpiperidine | 4.7 | 5.3 | 6.1 | 5 | 7 | 7 |
| POLYPROPYLENE + 0.5% benzophenone (commercial) | 4.5 | 5.2 | 5.6 | 8 | 7 | 50 |

The data tabulated above show that the excellent stabilizing action of the compounds of the present invention is in many instances well above the efficacy of the commercial products now in common use.

I claim:

1. An ester compound of the formula:

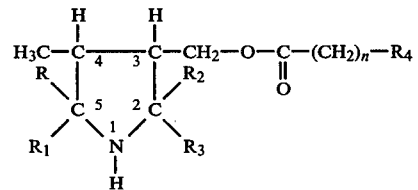

wherein R, $R_1$, $R_2$ and $R_3$ are methyl radicals, $R_4$ is hydrogen or a carboxyester radical which is the same as the esterified group which contains the pyrrolidine ring, and n is 4 or 17, $R_4$ being hydrogen where n is 17 and being a carboxyester which is the same as the esterified group which contains the pyrrolidine ring where n is 4.

2. A compound according to claim 1 which is adipoyl-bis(2,2,4,5,5-pentamethyl-pyrrolidine-3-methylol)-ester.

3. A compound according to claim 1 which is 2,2,4,5,5-pentamethyl-pyrrolidine-3-methylol-stearate.

4. A composition of matter comprising a polyolefin polymer and as an Ultra-Violet radiation stabilizer therefor from 0.5% to 0.9% by weight of an ester compound having the formula:

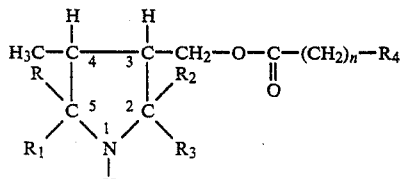

wherein R, $R_1$, $R_2$ and $R_3$ are methyl radicals, $R_4$ is hydrogen or a carboxyester radical which is the same as the esterified group which contains the pyrrolidine ring, and n is 4 or 17, $R_4$ being hydrogen where n is 17 and being a carboxyester which is the same as the esterified group which contains the pyrrolidine ring where n is 4.

5. A composition according to claim 4 wherein the ester is adipoyl-bis(2,2,4,5,5-pentamethyl-pyrrolidine-3-methylol)-ester.

6. A composition according to claim 4 wherein the ester is 2,2,4,5,5-pentamethyl-pyrrolidine-3-methylol stearate.

7. A method for stabilizing a polyolefin polymer against the noxious effects of Ultra-Violet radiation comprising adding to said polyolefin polymer from 0.5% to 0.9% by weight of an ester compound having the formula:

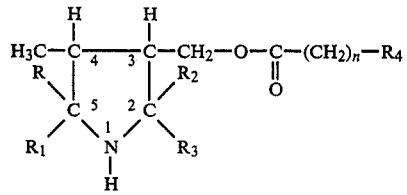

wherein R, $R_1$, $R_2$, and $R_3$ are methyl radicals, $R_4$ is hydrogen or a carboxyester radical which is the same as the esterified group which contains the pyrrolidine ring, and n is 4 or 17, $R_4$ being hydrogen where n is 17 and being a carboxyester which is the same as the esterified group which contains the pyrrolidine ring where n is 4 and forming a polyolefin polymer composition which is stable against the noxious effects of Ultra-Violet radiation.

* * * * *